United States Patent [19]

Hasty

[11] Patent Number: 5,022,387
[45] Date of Patent: Jun. 11, 1991

[54] ANTIEMBOLISM STOCKING USED IN COMBINATION WITH AN INTERMITTENT PNEUMATIC COMPRESSION DEVICE

[75] Inventor: James H. Hasty, Glenview, Ill.

[73] Assignee: The Kendall Company, Mansfield, Mass.

[21] Appl. No.: 424,842

[22] Filed: Oct. 20, 1989

Related U.S. Application Data

[63] Continuation of Ser. No. 94,368, Sep. 18, 1987, abandoned.

[51] Int. Cl.⁵ .............................................. A61H 9/00
[52] U.S. Cl. ..................................... 128/64; 128/24 R
[58] Field of Search ............................ 128/165, 424 R

[56] References Cited

U.S. PATENT DOCUMENTS

| | | | |
|---|---|---|---|
| 3,728,875 | 4/1973 | Hartigan et al. | 128/165 |
| 3,826,249 | 7/1974 | Lee | 128/24 R |
| 4,013,069 | 3/1977 | Hasty | 128/64 |
| 4,091,804 | 5/1978 | Hasty | 128/64 |
| 4,152,748 | 5/1979 | Arkans | 128/779 |
| 4,153,050 | 5/1979 | Bishop et al. | 128/64 |
| 4,156,425 | 5/1979 | Arkans | 128/24 R |
| 4,198,961 | 4/1980 | Arkans | 128/24 R |
| 4,202,325 | 5/1980 | Villari et al. | 128/24 R |
| 4,207,875 | 6/1980 | Arkans | 128/24 R |
| 4,207,876 | 6/1980 | Annis | 128/24 R |
| 4,253,449 | 3/1981 | Arkans et al. | 128/24 R |
| 4,280,485 | 7/1981 | Arkans | 128/24 R |
| 4,320,746 | 3/1982 | Arkans et al. | 128/24 R |
| 4,375,217 | 3/1983 | Arkans | 128/24 R |

OTHER PUBLICATIONS

Surgery, vol. 87, pp. 69-76, 1980.
Intermittent Sequential Pneumatic Compression of the Legs and Thromboembolism-Deterrent Stockings in the Prevention of Postoperative Deep Venous Thrombosis, Surgery, vol. 94, pp. 21-24, 1982.
LymphaPress. Venodyne.

Primary Examiner—Edgar S. Burr
Assistant Examiner—Lisa Malvaso
Attorney, Agent, or Firm—Alvin Isaacs

[57] ABSTRACT

A device for applying compressive pressures against a patient's limb comprising a stocking having circumferentially elastic boot portion which applies a compressive pressure against the limb which decreases from the ankle to a top of the stocking, an elongated pressure sleeve for enclosing a length of the patient's limb over the stocking, said sleeve having a plurality of separate fluid pressure chambers progressively arranged longitudinally along the sleeve from a lower portion of the limb to an upper portion of the limb proximal the patient's heart relative to said lower portion, a device for intermittently forming a plurality of fluid pressure pulses and a device for connecting the pressure pulses to chambers in the sleeve to apply a compressive pressure against the patient's limb by the sleeve which decreases from the lower to upper portions.

6 Claims, 6 Drawing Sheets

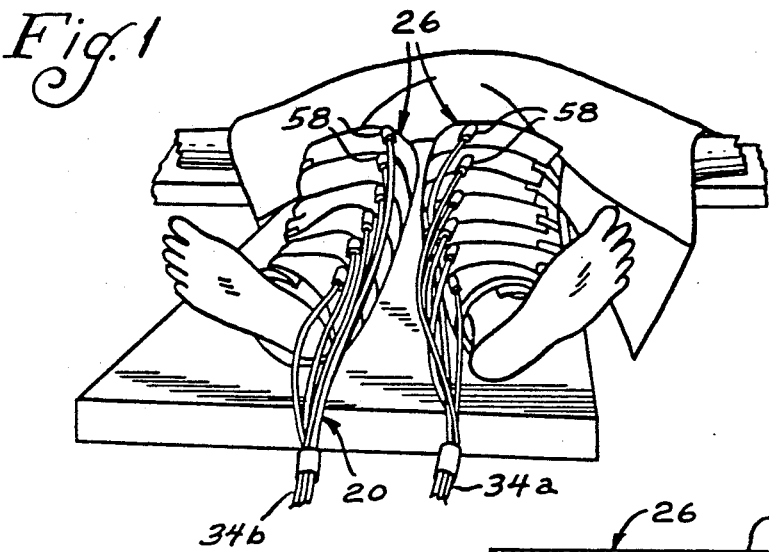
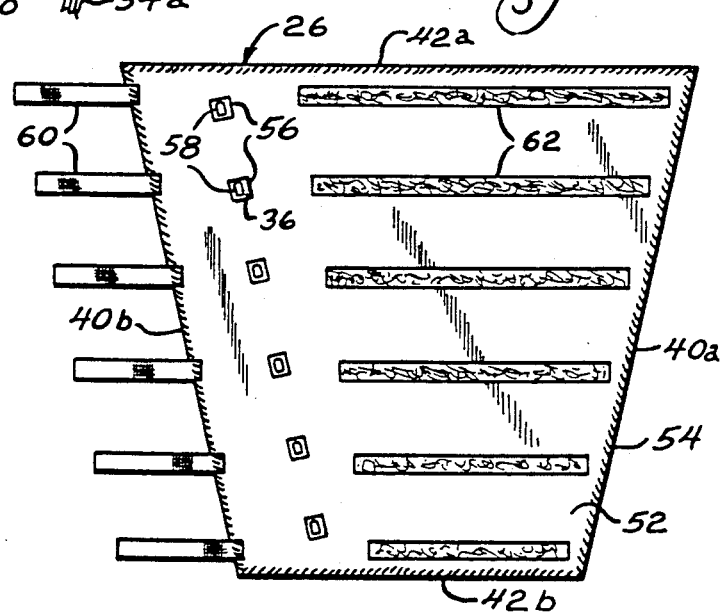
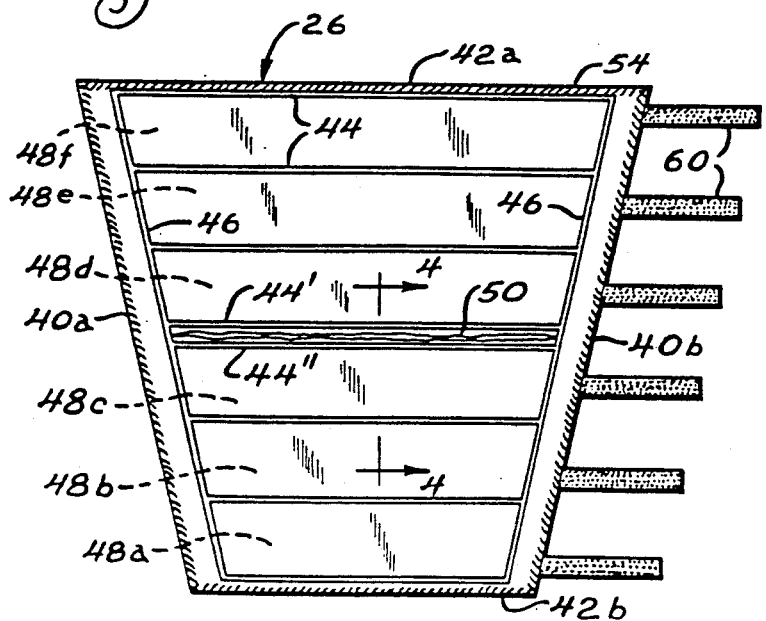

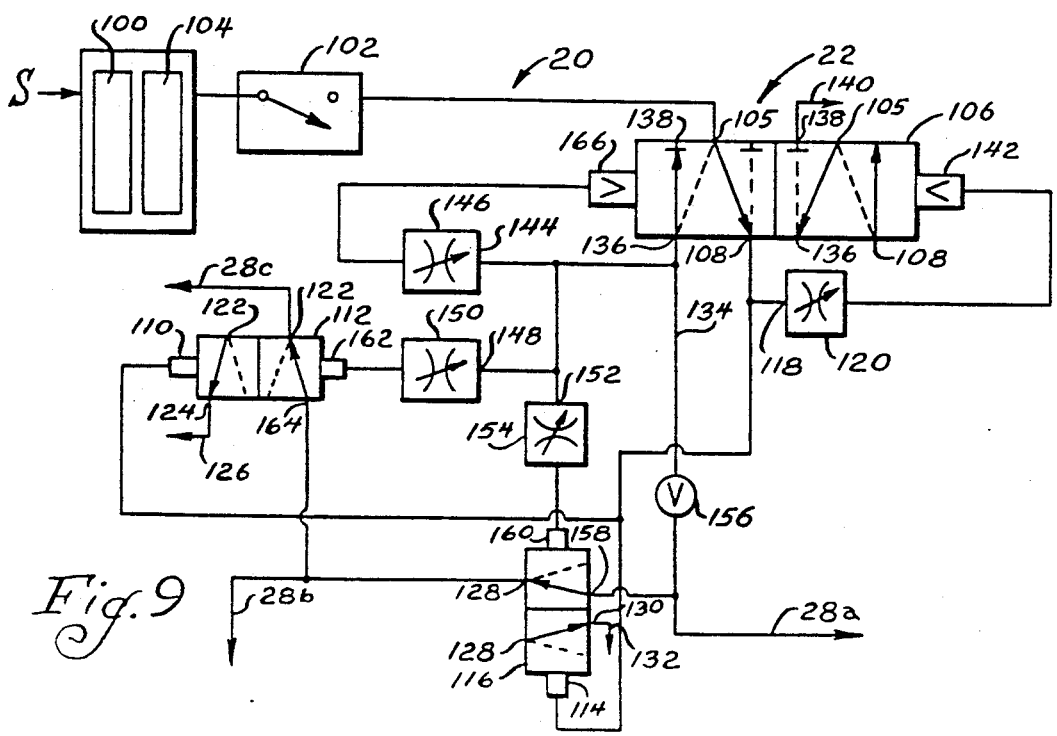

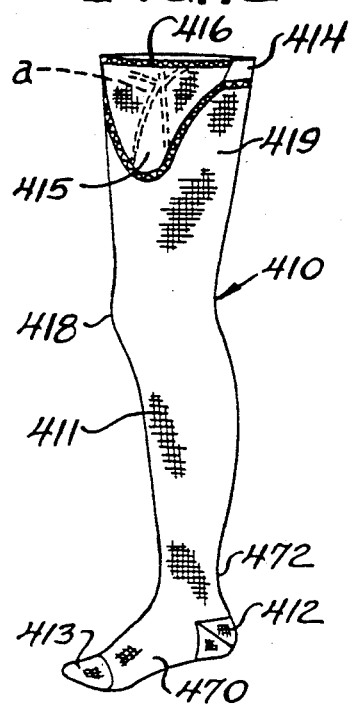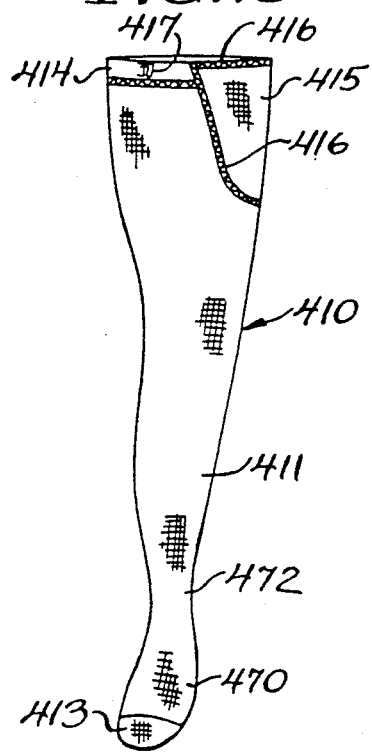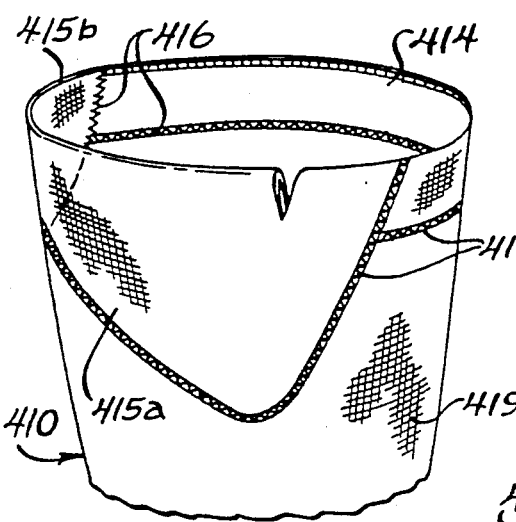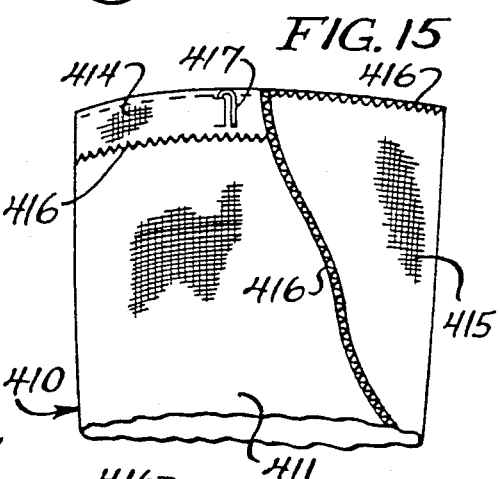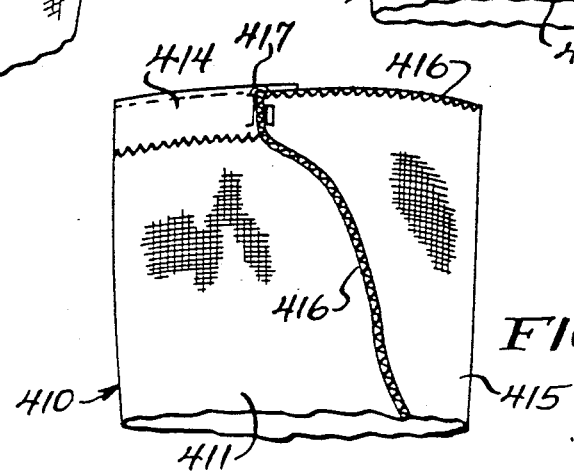

ANTIEMBOLISM STOCKING USED IN COMBIANTION WITH AN INTERMITTENT PNEUMATIC COMPRESSION DEVICE

This is a continuation of application Ser. No. 094,368, filed Sept. 8, 1987 now abandoned.

BACKGROUND OF THE INVENTION

The present invention relates to therapeutic and prophylactic devices, and more particularly to devices for applying compressive pressures against a patient's limb.

It is known that the velocity of blood flow in a patient's extremities, particularly the legs markedly decreases during confinement of the patient. Such pooling or stasis of blood is particularly pronounced during surgery, immediately after surgery, and when the patient has been confined to bed for extended periods of time. It is also known that stasis of blood is a significant cause leading to the formation of thrombi in the patient's extremities, which may have a severe deleterious effect on the patient, including death. Additionally, in certain patients it is desirable to move fluid out of interstitial spaces in extremity tissues, in order to reduce swelling associated with edema in the extremities.

The problem of postoperative deep venous thrombosis (DVT) and prophylactic regimens in its management have been described by the National Institutes of Health Concensus Development Conference on Prevention of Venous Thrombosis and Pulmonary Embolism. Clearly it is a problem of major concern, and several prophylactic modalities are available to help prevent its occurrence.

Modalities which have been identified to be effective in the reduction of postoperative DVT have been categorized on the basis of their mechanism of action in either preventing the hypercoagulable state or preventing stasis. While anticoagulants have been shown to be effective, they carry a risk of bleeding and wound hematoma. On the other hand, complications have not been associated with use of compression modalities, such as intermittent pneumatic compression (IPC) disclosed in U.S. Pat. No. 4,013,069 incorporated herein by reference, and graduated compression stockings disclosed in U.S. Pat. No. 3,728,875, incorporated herein by reference.

Combinations of prophylactic modalities to act on more than one component of Virchow's Triad have been utilized to achieve increased prophylactic effectiveness. The addition of graduated elastic compression to low dose heparin reduces the incidence of DVT compared to low dose heparin alone. The addition of dihydroergotamine to low dose heparin has been demonstrated to be more effective in reducing DVT than low dose heparin alone. The finding that certain combination prophylactic regimens are more effective than single modality regimens was indicated in a recently published meta-analysis of the literature which also emphasized the finding that the combination of graduated compression stockings before or after use of intermittent pneumatic compression (IPC) was more effective than IPC alone.

The foundation of this conclusion involves the original series of Nicolaides on IPC prophylaxis which indicated that IPC was as effective as low dose heparin for the time it was applied; however, after IPC was discontinued prophylactic protection diminished. Nicolaides AN, Fernandes JF, Pollock AV. Intermittent sequential pneumatic compression of the legs in the prevention of venous stasis and postoperative deep venous thrombosis. *Surgery*; 87:69-76. 1980. Further work conducted by Nicolaides subsequently combined graduated elastic compression after IPC to provide a "continuity" of prophylaxis so that when IPC was discontinued, graduated elastic compression stockings were applied and worn through the remainder of hospital stay. This combination regimen utilizing graduated elastic compression before and after the application of IPC (but not during use of IPC) indicated a result comparable to that of low dose heparin. One point demonstrated in this work on IPC is that effective prophylaxis requires a "continuity" of prophylaxis for the entire time the patient is at risk.

The physical methods of prophylaxis, including graduated elastic compression and IPC, have long been considered to act by promoting venous blood flow and thereby reducing the stasis component of Virchow's Triad. The action of IPC has been demonstrated to significantly increase blood flow pulsatility and enhance blood clearance from the soleal sinuses, the axial veins and the valve sinuses. More recently, it has been indicated that IPC stimulates fibrinolytic activity and, in addition, enhances prostacyclin generation.

Therefore, the prophylactic effectiveness of IPC is thought to arise from potentially two actions, a reduction of venous stasis by increasing venous flow pulsatility and reducing the hypercoagulable state. The prophylactic effectiveness of graduated elastic compression stockings is thought to be due primarily to its reduction of venous stasis by increasing linear blood flow velocity.

Previous efficacy studies on IPC as applied to the surgical patient have not used graduated elastic compression stockings simultaneously with IPC, even though some studies have used stockings sequentially with IPC to provide an improved continuity of prophylaxis.

SUMMARY OF THE PRESENT INVENTION

A principal feature of the present invention is the provision of a improved device for applying compressive pressures against a patients' limb.

The device of the present invention comprises, a stocking having a circumferentially elastic boot portion which applies a compressive pressure against the limb which decreases from the ankle to a top of the stocking, an elongated pressure sleeve for enclosing a length of the patients' limb over the stocking, said sleeve having a plurality of separate fluid pressured chambers progressively arranged longitudinally along the sleeve from a lower portion of the limb to an upper portion of the limb proximal the patients' heart relative to said lower portion, means for intermittently forming a plurality of fluid pressure pulses, and means for connecting the pressure pulses to chambers in the sleeve to apply a compressive pressure against the patients' limb by the sleeve which decreases from the lower to upper portions.

A feature of the present invention is that the device is a more effective prophylactic regimen than stockings or intermittent pneumatic compression taken above.

Further features will become more fully apparent in the following description of the embodiments of this invention and from the appended claims.

DESCRIPTION OF THE DRAWINGS

In the drawings:

FIG. 1 is a perspective view of a pair of compression sleeves used in the sequential intermittent compression device of the present invention;

FIG. 2 is a front plan view of a compression sleeve of FIG. 1;

FIG. 3 is a back plan view of the sleeve of FIG. 2;

FIG. 4 is a sectional view taken substantially as indicated along the line 4—4 of FIG. 3;

FIG. 5 is a schematic view of a manifold for use in connection with the device of FIG. 1;

FIG. 6 is a perspective view of the manifold for use with the device of FIG. 1;

FIG. 7 is a sectional view taken substantially as indicated along the line 7—7 of FIG. 6;

FIG. 8 is a graph illustrating pressure-time curves during operation of the compression device;

FIG. 9 is a schematic diagram of one embodiment of a pneumatic control circuit for the compression device;

FIGS. 12 and 13 illustrate respectively a typical stocking view from the inner leg side and the front;

FIG. 14 illustrate the top portion of a preferred form of circular knit stocking of the invention;

FIGS. 15 and 16 illustrate views of the top of a typical stocking before and after the upper thigh circumference has been adjusted;

DESCRIPTION OF THE PREFERRED EMBODIMENTS

Figure 10:
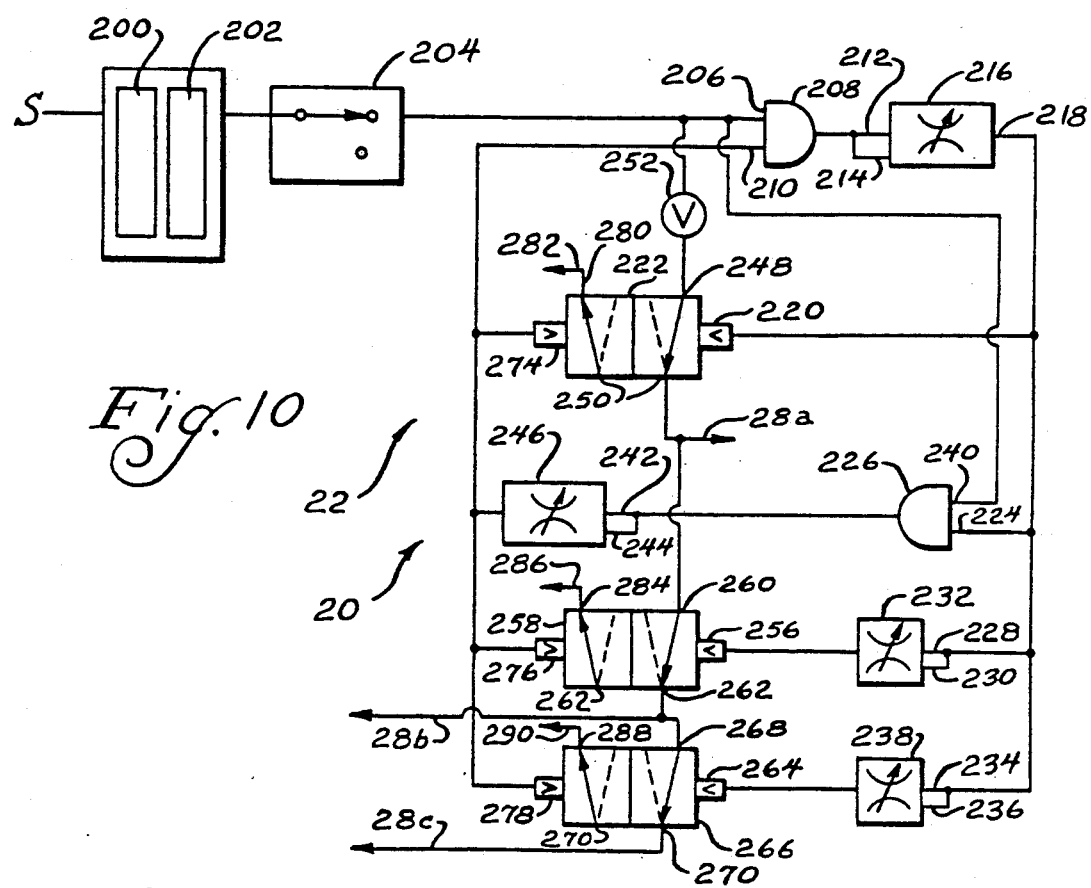
FIG. 10 is a schematic diagram of another embodiment of a pneumatic control circuit for the compression device.
Figure 11:
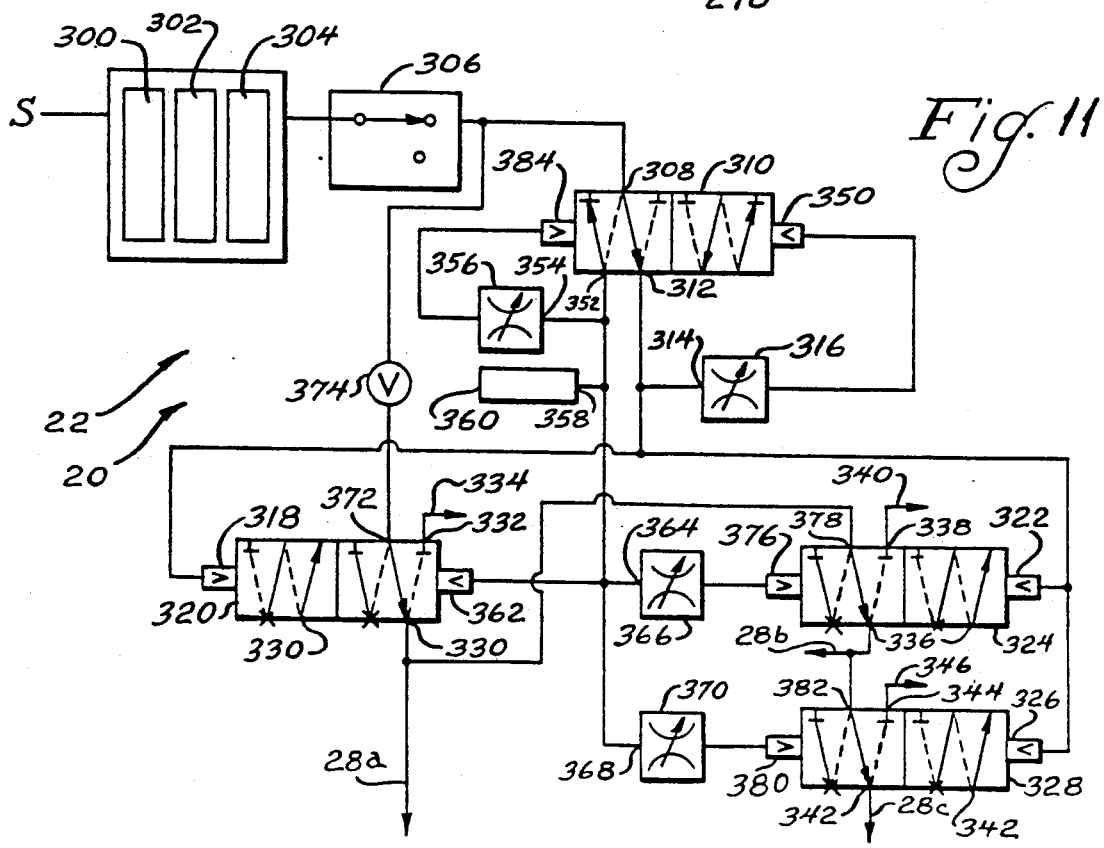
FIG. 11 is a schematic diagram of another embodiment of a pneumatic control circuit for the compression device.

Referring now to FIGS. 1, 6, and 9–11, there is shown a sequential intermittent compression device generally designated 20 for applying compressive pressures against a patient's extremities, such as the legs. The device 20 has a controller 22, as illustrated in FIGS. 9–11, a manifold 24, as shown in FIG. 6, and a pair of compression sleeves 26 for enclosing lengths of the patient's legs, as shown in FIG. 1. The controllers 22 of FIGS. 9–11 intermittently form a plurality of fluid pressure pulses from a source S of pressurized gas in a timed sequence during periodic compression or inflation cycles, and the pulses are separately applied to the manifold 24 of FIG. 6 through conduits 28a, 28b, and 28c at inlet ports of the manifold 24. The manifold 24 of FIG. 6 separates the pulses for passage to the separate sleeves 26 through conduits 34a and 34b which are separately connected to the sleeves, as shown in FIG. 1.

As shown in FIGS. 2–4, the sleeves 26 have a pair of flexible sheets 36 and 38 which are made from a fluid impervious material, such as polyvinyl chloride. The sheets 36 and 38 have a pair of side edges 40a and 40b, and a pair of end edges 42a and 42b connecting the side edges 40a and b. As shown in FIGS. 3 and 4, the sheets have a plurality of laterally extending lines 44, such as lines of sealing, connecting the sheets 36 and 38 together, and a pair of longitudinally extending lines 46, such as lines of sealing, connecting the sheets 36 and 38 together and connecting ends of the lateral lines 44, as shown. The connecting lines 44 and 46 define a plurality of contiguous chambers 48a, 48b, 48c, 48d, 48e, and 48f which extend laterally in the sheet, and which are disposed longitudinally in the sleeve between the end edges 42a and 42b. When the sleeve is placed on the patient's leg, the lowermost chamber 48a is located on a lower part of the leg adjacent the patient's ankle, while the uppermost chamber is located on an upper part of the leg adjacent the mid-thigh.

In a preferred embodiment, the side edges 40a and 40b and the connecting lines 46 are tapered from the end edge 42a toward the end edge 42b. Thus, the sleeve 26 has a reduced configuration adjacent its lower end to facilitate placement of the sleeve on the more narrow regions of the leg adjacent the patient's ankles. Moreover, it will be seen that the connecting lines 44 and 46 define chambers having volumes which progressively increase in size from the lowermost chamber 48a to the uppermost chamber 48f. The relative size of the chambers facilitates the device in conjunction with orifices to develop a compressive pressure gradient during the compression or inflation cycles which decreases from a lower part of the sleeve adjacent the end edge 42b toward an upper part of the sleeve adjacent the end edge 42a.

As illustrated in FIGS. 3 and 4, the adjoining chambers 48c and 48d may have their adjacent portions defined by spaced connecting lines 44' and 44" which extend laterally in the sleeve between the connecting lines 46. The sheets 36 and 38 may be severed, such as by slitting, along a line 50 between the lines 44' and 44" to separate the adjoining chambers 48c and 48d. As shown, the severence line 50 may extend the width of the chambers between the connecting lines 46. The line 50 permits free relative movement between the adjoining chambers when the sleeve is inflated to prevent hyperextension of the leg during operation of the device, and also facilitates sizing of the sleeve to the leg of a particular patient.

The sleeve 26 may have one or more sheets 52 of a soft flexible material for covering the outside of the fluid impervious sheets 36 and 38 relative the patient's leg. The sheets 52 may be made of any suitable material, such as Tyvek, a trademark of E.I. du Pont de Nemours, and provide an aesthetically pleasing and comfortable outer surface for the sleeve 26. The sheets 52 may be attached to the sheets 36 and 38 by any suitable means, such as by lines 54 of stitching along the side edges 40a and b and end edges 42a and b which pass through the sheets 52 and sheets 36 and 38 to secure the sheets together. As shown in FIG. 2, the sheets 52 may have a plurality of openings 56 to receive a plurality of connectors 58 which are secured to the sheet 36 and which communicate with the separate chambers in the sleeve 26. As illustrated in FIG. 1, the connectors 58 are secured to the conduits 34a and b, such that the conduits separately communicate with chambers in the sleeve through the connectors 58.

As best shown in FIGS. 2 and 3, the sleeves 26 may have a plurality of hook and loop strips 60 and 62, respectively, to releasably secure the sleeves about the patient's legs. The hook strips 60 extend past one of the side edges 40b of the sleeve, while the loop strips 62 are secured to the outside of the outer sheet 52. During placement, the sleeves 26 are wrapped around the patient's legs, and the hook strips 60 are releasably attached to the associated loop strips 62 on the outside of the sleeves in order to secure the sleeves on the legs and confine movement of the sleeves away from the patient's legs when inflated during operation of the device.

As will be further discussed below, the controllers 22 of FIGS. 9-11 intermittently form a plurality of fluid pressure pulses in a timed sequence during the periodic inflation or compression cycles, in order to sequentially initiate inflation of different chambers in the sleeves. In the particular embodiments shown, the controllers 22 form three timed pressure pulses during each inflation cycle which are utilized to inflate the six chambers in each of the sleeves, such that each pulse is associated with two chambers in the sleeves. However, it will be understood that a timed pulse may be formed for each of the chambers in the sleeves, and that the number of timed pulses may be varied in accordance with the particular type of sleeve being used in the device.

A graph of the pressures P formed in the chambers of each sleeve with respect to time T is shown in FIG. 8. The time $t_0$ designates the start of an inflation cycle when a first pressure pulse is formed by the controller, and the first pulse is applied to the two lowermost chambers in each of the sleeves at that time. As will be discussed below, the manifold separates the first pulse, and connects the separated pulses to the two lowermost chambers 48a and 48b, as designated on the corresponding curves of FIG. 8. As shown, the pulse applied to the lowermost chamber 48a has a faster pressure rise time than the pulse applied to the adjoining upper chamber 48b, such that the rate of change of pressure in the lowermost chamber 48a is greater than the rate of change of pressure in the adjoining chamber 48b. Accordingly, the sleeve will exert a compressive pressure gradient against the limb which decreases from the lowermost chamber 48a to the adjoining upper chamber 48b in the lower set of adjoining chambers until the maximum pressure in the two chambers is reached and the chambers are filled.

The controller forms the second pressure pulse at the time $t_1$ during the inflation cycle, and inflation of the third and fourth chambers 48c and 48d in the sleeve is initiated at this time. It will be seen that the device initiates inflation of the third and fourth chambers while the first and second chambers are still being filled from the first pressure pulse. The second pressure pulse is also separated by the manifold for the set of the third and fourth adjoining chambers which have different pressure rise times, as shown, with the pressure rise time for the third chamber 48c being greater than the pressure rise time for the fourth chamber 48d. Thus, as in the case of the set of lowermost adjoining chambers, the rate of pressure change in the third chamber 48c is greater than the rate of pressure change in the fourth chamber 48d, such that the set of intermediate adjoining chambers also exerts a compressive pressure gradient against the limb which decreases from the third to fourth chamber. Additionally, it will be seen that the rates of pressure increases in the third and fourth chambers are less than those in the corresponding first and second chambers. Accordingly, while the third and fourth chambers are being filled, the pressures applied by the third and fourth chamber of the sleeve are less than the pressures applied by the first and second chambers, and the first, second, third, and fourth chambers thus exert a compressive pressure gradient which decreases from the lowermost chamber 48a through the fourth chamber 48d.

At the time $t_2$ the controller initiates formation of the third pressure pulse for the fifth and sixth chambers 48e and 48f. As before, the pressure rise time in the fifth chamber 48e is greater than that in the uppermost sixth chamber 48f, such that the rate of change of pressure in the fifth chamber is greater than the rate of change of pressure in the sixth chamber. Accordingly, the set of adjoining uppermost chambers applies a compressive pressure gradient against the patient's limb which decreases from the fifth to sixth chambers. As shown, the pressure rise times in the fifth and sixth chambers are less than those in the four lowermost chambers, and while the fifth and sixth chambers are being filled, the pressure in these uppermost chambers is less than the pressures in the four lowermost chambers. Thus, the sleeve applies a compressive pressure gradient against the patient's limb which decreases from the lowermost chamber 48a to the uppermost chamber 48f in the sleeve. Once reached, the maximum pressures in the two lowermost chambers 48a and 48b are generally maintained throughout the inflation cycle while the remaining chambers are still being filled. Similarly, when the maximum pressures are attained in the third and fourth chambers 48c and 48d, these pressures are generally maintained while the pressures are increased in the uppermost fifth and sixth chambers 48e and 48f. Maintenance of pressures in a lower set of chambers may be subject to slight diminution when inflation of an upper set of chambers is initiated. Finally, when the maximum pressures are obtained in the fifth and sixth chambers, all of the chambers have achieved their maximum pressures during the inflation cycle. In a preferred form, as shown, the maximum pressures attained in a lower set of chambers is greater than those in an upper set of chambers, although the maximum pressures in the various sets may approach a comparable value, as desired. In this manner, the device intermittently applies a compressive pressure gradient by the sleeve during the inflation cycles which decreases from a lower part of the sleeve to an upper part of the sleeve.

The controller initiates a deflation cycle at the time $t_3$ when the air is released from the chambers, in order to deflate the chambers and release the pressures applied by the sleeves against the limb.

The deflation cycle continues through a period of time until the subsequent time $t_0$, when the controller again initiates formation of the first pressure pulse during a subsequent inflation cycle. The controller thus intermittently forms a plurality of pressure pulses in a timed sequence for inflating the sleeves during periodic inflation cycles, and intermittently releases pressure from the sleeves during periodic deflation cycles between the inflation cycles.

As will be seen below, the time intervals between initiation of the sequential pressure pulses, i.e., between times $t_0$ and $t_1$, and between times $t_1$ and $t_2$, is adjustable to modify the timed relationship of the pulse sequence. Additionally, the time interval elapsed during the inflation cycle, i.e., the time interval between times $t_0$ and $t_3$ is also adjustable to modify the duration of the periodic inflation cycles. Moreover, the time interval during the deflation cycles, i.e., the time interval between times $t_3$ and $t_0$, is adjustable to modify the duration of the periodic deflation cycles. Thus, the various time intervals associated with applying and removing the pressure gradients by the sleeves are suitably adjustable according to the physiology of the patient.

The controller 22 and manifold 24 are illustrated in schematic form in FIG. 5. The controller 22 forms and applies the first pressure pulse to a first manifold section 64a through the conduit 28a. The manifold section 64a separates the first pulse through a pair of orifices 66a and 66b, and simultaneously supplies the separated first pulses to separate manifold sections 68a and 68b. In turn, the manifold section 68a further separates the pulse through orifices or ports 70a and 70b, which permit free passage of gas therethrough or are of equal size, and simultaneously supplies the separated pulses to the two lowermost chambers 48a in the pair of sleeves respectively through the associated conduits 34a and 34b. Similarly, the manifold section 68b separates the pulse through similar orifices or ports 70c and 70d, and simultaneously supplies the separated pulses to the two second chambers 48b in the pair of sleeves through the associated conduit 34a and 34b. As shown, the effective size of the orifice 66a is substantially greater than the effective size of the orifice 66b in the manifold section 64a, such that the rate of flow of gas to the manifold section 68a is greater than the rate of flow of gas to the manifold section 68b. However, the effective sizes of the orifices 70a, b, c, and d in the sections 68a and b are such that the rate of gas flow through the section 68a to the two lowermost chambers 48a in the sleeves will be the same, while the rate of gas flow through the section 68b to the two second chambers 48b in the sleeves will also be the same although less than that to the two lowermost chambers. Accordingly, the rate of gas flow through the section 64a to the two lowermost chambers 48a will be greater than the rate of gas flow through the section 64a to the two second chambers 48b, although the rate of flow to the two lowermost chambers 48a will be the same and the rate of flow to the second chambers 48b will be the same. In this manner, the lowermost chambers are filled at a greater rate than the second chambers and have faster pressure rise times, such that a compressive pressure gradient is produced in the first and second chambers of the separate sleeves which decreases from the first chamber 48a to the second chamber 48b. The relative rate of gas flow through the manifold section 64a may be controlled by suitable selection of the internal diameters of the orifices 66a and 66b.

The controller 22 forms and supplies the second pulse in the sequence to the manifold section 64b. The section 64b separates the second pulse through a pair of orifices 66c and 66d, with the orifice 66c having an effective greater size than the orifice 66d, such that the resulting pulse supplied to the manifold section 68c will have a greater flow rate than the pulse supplied to the section 68d. As shown, the section 68c separates the pulse through orifices 70e and 70f, and simultaneously supplies the separated pulses to the two third chambers 48c in the pair of sleeves through the associated conduits 34a and 34b. The effective sizes of the orifices 70e and f are such that the rate of gas flow into the third chambers 48c of the two sleeves will be approximately the same. Similarly, the section 68d separates the pulse supplied to this section through orifices 70g and 70h, and simultaneously supplies the resulting separated pulses to the two fourth chambers 48d of both sleeves through the associated conduits 34a and 34b. Again, the effective sizes of the orifices 70g and 70h are such that the rate of gas flow into the fourth chambers through conduit 34a and 34b will be approximately the same. However, since the effective size of orifice 66c is greater than that of orifice 66d, the flow rate through section 68c to the third chambers 48c is greater than that through the section 68d to the fourth chambers 48d. Thus, the pressure rise times in the third chambers of the sleeves is greater than those in the fourth chambers of the sleeves, and the third and fourth chambers apply a compressive pressure gradient against the patient's limb which decreases from the third to fourth chambers. As previously discussed in connection with FIG. 8, the second pressure pulse is formed by the controller 22 after formation of the first pulse, and the pressure rise times in the chambers decrease upwardly along the sleeve. Accordingly, the timed pulses supplied to the lower four chambers in the sleeves result in application of a compressive pressure against the patient's limb which decreases from the lowermost chamber 48a to the fourth chamber 48d.

As will be discussed below, the controller 22 forms the second pressure pulse, which is supplied to the manifold through the conduit 28b, from the first pressure pulse which is supplied to the manifold through the conduit 28a. The controller forms the second pulse in this manner to produce the progressively decreasing pressure rise times in the chamber sets and to prevent a possible inversion of the pressure gradients applied by the sleeves, since the second pressure pulse will not be formed unless the first pulse has been properly formed.

However, since both manifold sections 64a and b are supplied from the first pulse after the second pulse has been formed, a lesser filling pressure is available to the section 64b than was initially available to the section 64a before formation of the second pulse. Thus, the effective size of the orifice 66c of section 64b is made greater than that of the corresponding orifice 66a in the section 64a to obtain the desired comparable, although decreasing, pressure rise times in the corresponding first and third chambers. Similarly, the orifice 66d of section 64b, although smaller than the orifice 66c in the same section, has an effective greater size than the corresponding orifice 66b in the section 64a to obtain the desired comparable and decreasing pressure rise times in the corresponding second and fourth chambers. Thus, although the controller supplies gas for the second pressure pulse to the section 64b from the first pressure pulse, the effectively increased orifice sizes in the section 64b provide separate filling rates for the third and fourth chambers which are comparable to, but preferably less than, the separate filling rates for the first and second chambers of the sleeves respectively, such that the pressure rise times in the third and fourth chambers are comparable to, but preferably less than, the corresponding pressure rise times in the first and second chamber as previously discussed in connection with FIG. 8.

The controller then forms the third pulse, and supplies this pulse to the manifold section 64c through the conduit 28c. The section 64c separates the third pulse through flow control orifices 66e and 66f having effective different sizes, and simultaneously supplies the separated pulses to the manifold sections 68e and 68f. In turn, the sections 68e and f separate the pulses through orifices 70i, 70j, 70k, and 70 l, and simultaneously supplies separated pulses to the fifth and sixth chambers 48e and 48f, respectively, of both sleeves through the associated conduits 34a and 34b. Accordingly, the rate of gas flow from the section 64c through orifice 66e to the fifth chambers 48e is greater than that through the orifice 66f to the uppermost sixth chambers 48f, such that the pressure rise times in the two fifth chambers of the sleeves is greater than that in the uppermost sixth chambers of the sleeves. Thus, the fifth and sixth chambers apply a compressive pressure gradient against the patient's limb which decreases from the fifth to sixth chambers. Additionally, since the third pressure pulse is delayed relative the first two pressure pulses and since the pressure rise times in the fifth and sixth chambers is less than the corresponding lower chambers, the pressures applied by the fifth and sixth chambers against the patient's limb while being filled are less than those applied by the lower four chambers, as discussed in connection with FIG. 8, and the six chambers of the two sleeves thus combine to apply a compressive pressure gradient against the limbs which decreases from the lowermost chambers 48a to the uppermost chambers 48f of the sleeves.

As will be discussed below, the third pressure pulse supplied by the controller 22 through the conduit 28c is formed from the second pulse supplied through the conduit 28b in order to prevent an inversion of the desired pressure gradient and to provide the decreasing pressure rise times. Accordingly, the effective size of the orifice 66e in the section 64c is made greater than the effective size of the orifice 66c in the section 64b, while the effective size of the orifice 66f in the section 64c is greater than the effective size of the orifice 66d in the section 64b, which also permits the device to maintain the desired pressures in the lower chambers while filling the uppermost chambers. Thus, although the lower four sleeve chambers are driven from the first and second pulses and the third pulse is driven from the second pulse, the effective increased size of the orifices in the section 64c relative the sections 64b and 64a provides comparable, but decreased, pressure rise times in the uppermost fifth and sixth chambers, in a manner as previously described.

Referring now to FIGS. 5-7, the first, second, and third pressure pulses are supplied to a manifold housing 72 through the conduits 28a, b, and c, respectively. The manner in which the first pressure pulse is separated by the manifold 24 for filling the first and second chambers 48a and 48b will be described in conjunction with FIG. 7. The first pulse is supplied through the conduit 28a and inlet port 73, to a channel 74 in the housing 72, and the first pressure pulse is then separated through the orifices 66a and 66b in the housing 72. As shown, the internal diameter of the orifice 66a is greater than the internal diameter of the orifice 66b, such that the rate of flow of gas from the channel 74 into the housing channel 76 is greater than the rate of flow from the channel 74 into the housing channel 78. The pulse formed in the channel 76 is separated through orifices or outlet ports 70a and 70b having an internal diameter of approximately the same size, or of sufficiently large size to prevent obstruction to passage therethrough, and the separated pulses from orifices 70a and b are then separately supplied to the two lowermost chambers 48a of the pair of sleeves through the associated conduits 34a and 34b. Similarly, the pulse formed in the channel 78 is separated by the orifices or outlet ports 70c and 70d having an internal diameter of approximately the same size as the orifices 70a and 70b or of non-obstructive size. The separated pulses pass from the orifices 70c and d through the associated conduits 34a and b to the two second chambers 48b in the pair of sleeves.

In this manner, the first pulse passing through the inlet port 73. is separated into separate pulses in the channels 76 and 78, with the pulse in the channel 76 having a faster pressure rise time than the pulse in the channel 78. In turn, the pulse in the channel 76 is separated and supplied to the two lowermost chambers in the pair of sleeves, while the pulse in the channel 78 is separated and supplied to the two second channels in the pair of sleeves. Referring to FIGS. 6 and 7, the second pressure pulse supplied to the manifold 24 through the conduit 28b is separated in a similar manner through a series of channels and orifices for filling the third and fourth chambers. Similarly, the third pulse, supplied to the manifold 24 through the conduit 28c, is separated by interconnected channels and orifices, with the resulting pulses being supplied to the uppermost fifth and sixth chambers. As shown, the manifold may have a pressure relief valve or pressure indicating device 81 secured to the housing 72 and communicating with the channel 74 or with any other channel or port, as desired.

In a preferred form, the controller 22 is composed of pneumatic components, since it is a preferred procedure to minimize electrical components in the potentially explosive environment of an operating room. Referring to FIG. 9, the controller 22 has a regulator 100 connected to the source S of pressurized gas in order to lower the supply pressure and drive the controller circuitry. The regulator 100 is connected to a two-position switch 102 through a filter 104. When the switch 102 is placed in an off condition, the gas supply is removed from the circuitry components, while the switch connects the supply to the components when placed in its on condition.

When the switch 102 is turned on, the air supply passing through the switch 102 is connected to port 105 of a two-position or shift valve 106. In a first configuration of the valve, the supply is connected by the valve through the valve port 108 to port 110 of shift valve 112, to port 114 of shift valve 116, and to port 118 of a positive output timer 120. Actuation of the shift valve 112 at port 110 causes the valve 112 to connect its port 122 to valve port 124 and exhaust line 126. Similarly, actuation of the shift valve 116 at port 114 causes the valve 116 to connect its port 128 to port 130 and exhaust line 132. Also, the valve 106 connects the line 134 through its ports 136 and 138 to the exhaust line 140.

Accordingly, when the shift valve 106 connects the gas supply through its ports 105 and 108, the controller initiates a deflation cycle during which gas passes from the sleeve chambers to the various exhaust lines, as will be seen below. At this time, the supply also initiates the timer 120 which controls the duration of the deflation cycle. The timer 120 is adjustable to modify the duration of the deflation cycle, and when the timer 120 times out, the timer actuates the shift valve 106 at port 142 to initiate an inflation cycle.

The actuated valve 106 connects the gas supply through ports 105 and 136 to port 144 of a positive output timer 146, to port 148 of a positive output timer 150, to port 152 of a positive output timer 154, and through the flow control valve 156 to port 158 of shift valve 116. The actuated valve 106 also disconnects its port 105 from port 108. The flow control valve 156 serves to reduce the relatively high pressure utilized to actuate the pneumatic components of the circuitry to a lower pressure for inflating the chambers in the sleeves.

The gas supply passing through line 134 and valve 156 also passes through the conduit 28a to the manifold. Accordingly, the first pressure pulse is formed through the conduit 28a for filling the first and second chambers 48a and b of the sleeves at this time. When the timer 154 times out, the gas supply is connected by the timer to port 160 of shift valve 116, which causes the valve 116 to connect its port 158 to port 128. Thus, the gas supply passing through flow control valve 156 is connected through the shift valve 116 to the conduit 28b, and the second pressure pulse is formed and supplied to the manifold for inflating the third and fourth chambers of the sleeves. It will be seen that the controller forms the second pressure pulse from the first pressure pulse which is continuously supplied to the manifold through the conduit 28a. The time interval between initiation of the first and second pressure pulses, respectively supplied through the conduits 28a and 28b, is controlled by the adjustable timer 154. Accordingly, the duration between formation of the first and second pressure pulses may be modified by simple adjustment of the timer 154.

When the timer 150 times out, the timer 150 connects the gas supply through the timer to port 162 of shift valve 112, causing the valve to connect its port 164 to port 122. The gas supply then passes through the ports 164 and 122 of shift valve 112 to the conduit 28c and manifold in order to inflate the fifth and sixth chambers of the sleeves. Accordingly, the third pressure pulse supplied to the manifold is formed at this time by the control circuitry. It will be seen that the controller forms the third pressure pulse from the second pressure pulse supplied to conduit 28b, which in turn is formed from the first pressure pulse, as previously described, and the first and second pressure pulses are continuously supplied to the manifold after the third pressure pulse is passed through conduit 28c. The time interval between initation of the second and third pulses is determined by the adjustable timer 150, and the timer 150 may be adjusted to suitably modify the duration between the third pulse and the earlier pulses. Accordingly, the controller 22 forms a timed sequence of pressure pulses, with the time intervals between the sequential pressure pulses being adjustable, as desired.

When the timer 146 times out, the timer 146 connects the gas supply through the timer to port 166 of shift valve 106. At this time, the shift valve 106 again connects its port 105 to port 108, and disconnects the port 105 from port 136 of the valve, while the timer 120 is again actuated to begin a deflation cycle. It will be seen that the timer 146 controls the duration of the inflation cycles, since the deflation cycles are initiated when the timer 146 times out. The timer 146 also may be suitably adjusted to modify the duration of the inflation cycles.

As previously discussed, when the deflation cycles are initiated, the port 122 of shift valve 112 is connected to valve port 124 and the exhaust line 126. Thus, the two uppermost chambers 48e and 48f in the sleeves are deflated through the conduit 28c and the exhaust line 126 at this time. Similarly, when the valve 116 is actuated at port 114, the port 128 of shift valve 116 is connected to valve port 130 and exhaust line 132, such that the third and fourth chambers 48c and 48d are deflated through conduit 28b and the exhaust line 132. Finally, the shift valve 106 also connects its port 136 to port 138, such that the two lowermost chambers 48a and 48b are deflated through conduit 28a, valve ports 136 and 138, and exhaust line 140. In this manner, the various chambers in the sleeves are deflated during the deflation cycle. Referring to FIG. 5, it will be apparent that the pressure gradient, which decreases from a lower part of the sleeve to an upper part of the sleeve, is maintained during the deflation cycle, since the orifices in the section 64c are effectively larger than the corresponding orifices in the section 64b, while the orifices in the section 64b are effectively larger than the corresponding orifices in the section 64a. Thus, the two uppermost chambers 48e and f deflate through the orifices 66e and 66f and conduit 28c at a greater rate than the third and fourth chambers 48c and d through the orifices 66c and 66d in section 64b and conduit 28b. Similarly, the third and fourth sleeve chambers deflate at a greater rate than the two lowermost chambers 48a and b through orifices 66a and 66b in section 64a and conduit 28a. Accordingly, the compressive pressure gradient is maintained during inflation and deflation of the sleeves.

Referring again to FIG. 9, it will be seen that the controller 22 intermittently forms the first, second, and third pressure pulses in a timed sequence during periodic inflation or compression cycles of the device. Also, the controller intermittently deflates the chambers in the sleeve during periodic deflation or decompression cycles between the periodic inflation cycles.

Another embodiment of the controller 22 of the present invention is illustrated in FIG. 10. In this embodiment, the source of pressurized gas S is connected to a regulator 200, a filter 202, and an on-off switch 204, as described above. When the switch 204 is placed in its off configuration, the gas supply S is removed from the pneumatic components of the controller, while the supply S is connected to the components when the switch is placed in its on configuration.

When the switch 204 is turned on, the air supply S is connected to port 206 of not gate 208. When pressure is absent from port 210 of gate 208, the supply passes through port 206 of gate 208 to inlet ports 212 and 214 of a negative output timer 216. The supply actuates timer 216 at its port 212, and the supply passes through port 214 of the timer to its outlet port 218. In turn, the supply is connected to port 220 of shift valve 222, to port 224 of not gate 226, to ports 228 and 230 of a positive output timer 232, and to ports 234 and 236 of a positive output timer 238. The pressure supply at port 224 of gate 226 prevents the gate 226 from connecting port 240 of the gate 226 to ports 242 and 244 of a negative output timer 246.

The supply at valve port 220 actuates shift valve 222 which connects its port 248 to port 250, and thus the gas supply from switch 204 passes through the flow control valve 252, and ports 248 and 250 of shift valve 222, to the conduit 28a and manifold. The flow control valve 252 reduces the relatively high pressure of the gas supply, which is utilized to actuate the pneumatic components of the controller 22, to a lower pressure for inflation of the chambers in the sleeve. The conduit 28a is connected through the manifold to the two lowermost sleeve chambers 48a and b, as previously described. Thus, the device forms the first pressure pulse for filling the two lowermost chambers of the sleeves at the start of the inflation cycle.

When the positive output timer 232 times out, the timer 232 connects the gas supply from its port 230 to port 256 of shift valve 258, which then connects its port 260 to port 262. Thus, the actuated valve 258 connects the gas supply from the conduit 28a through its ports 260 and 262 to the conduit 28b and manifold for inflating the third and fourth chambers 48c and d of the sleeves, and forms the second pressure pulse from the first pressure pulse at this time, with the time interval between formation of the first and second pulses being controlled by the timer 232. As before, the duration between the first and second pulses may be modified by suitable adjustment of the timer 232.

When the positive output timer 238 times out, the timer 238 connects the supply from its port 236 to port 264 of shift valve 266. The actuated valve 266 connects its port 268 to port 270, and thus connects the gas supply from conduit 28b through the valve ports 268 and 270 to the conduit 28c and manifold. Thus, the valve 266 forms the third pressure pulse from the second pulse at this time for inflating the uppermost fifth and sixth chambers 48e and f in the sleeves. As before, the time interval between the third pulse and earlier pulses is controlled by the timer 238, and the duration between the pulses may be modified by suitable adjustment of the timer 238. It is noted at this time that the pneumatic components of the controller 22 are actuated by a portion of the circuitry which is separate from the gas supply passing through valve 252, and the conduits 28a, 28b, and 28c to the manifold and sleeves.

When the negative output timer 216 times out, the time 216 removes the supply from port 220 of shift valve 222, from port 224 of gate 226, from ports 228 and 230 of timer 232, and from ports 234 and 236 of timer 238. The absence of pressure at port 224 of gate 226 causes the gate to pass the supply through gate port 240 to ports 242 and 244 of the negative output timer 246 which initiates the start of the deflation cycle. Conversely, the timer 216 initiates and controls the duration of the inflation cycle, and the duration of the inflation and deflation cycles may be modified by suitable adjustment of the timers 216 and 246, respectively.

When the timer 246 is actuated at its port 242, the timer 246 passes the gas supply from its port 244 to port 210 of gate 208, to port 274 of shift valve 222, to port 276 of shift valve 258, and to port 278 of shift valve 266. The pressure at port 210 of gate 208 causes the gate 208 to remove the supply from the ports 212 and 214 of the inflation timer 216. At the same time, the pressure at port 274 of shift valve 222 actuates the valve which connects its port 250 to port 280 and the exhaust line 282. Accordingly, the lowermost sleeve chambers and 48a and b are connected by valve 222 to the exhaust line 282 through conduit 28a, and valve ports 250 and 280 of shift valve 222. Similarly, the pressure of port 276 of shift valve 258 actuates this valve which connects its port 262 to port 284 and the exhaust line 286. Thus, the third and fourth chambers 48c and d of the sleeves are deflated through conduit 28b, ports 262 and 284, and the exhaust line 286. Finally, the pressure at valve port 278 actuates shift valve 266 which connects its port 270 to port 288 and the exhaust line 290. Accordingly, the uppermost fifth and sixth chambers 48e and f of the sleeves are deflated through conduit 28c, valve ports 270 and 288 and the exhaust line 290. It will be seen that all the chambers in the sleeves are simultaneously deflated through the various exhaust lines 282, 286, and 290, and the compressive pressure gradient which decreases from the lower to upper part of the sleeves is maintained during deflation of the sleeves by the variously sized manifold orifices, in a manner as previously described.

When the deflation timer 246 times out, the timer 246 removes the supply from port 210 of gate 208, as well as ports 274, 276, and 278 of valves 222, 258, and 266, respectively, and the gas supply is again connected from port 206 of gate 208 to ports 212 and 214 of timer 216 to initiate another inflation cycle. It will thus be seen that the controller 22 of FIG. 10 also operates to intermittently form a plurality of pressure pulses in a timed sequence for inflating the sleeves during periodic inflation cycles, and intermittently deflate the filled sleeve chambers during periodic deflation cycles between the inflation cycles.

Another embodiment of the sequential intermittent compression controller of the present invention is illustrated in FIG. 11. As before, the source S of pressurized gas is connected to a regulator 300, after which the source passes through a primary filter 302 and an oil filter 304 to a two-position switch 306. Again, when the switch is placed in its off condition, the source or supply is removed from the pneumatic components of the circuitry, while the source is connected to the components when the switch 306 is placed in its on condition.

When the switch is turned on, the supply is connected through the switch 306 to port 308 of shift valve 310. During the deflation cycles, the valve 310 connects its port 308 to port 312, such that the gas supply is connected to port 314 of a positive output timer 316, to port 318 of shift valve 320, to port 322 of shift valve 324, and to port 326 of shift valve 328.

The actuated shift valve 320 connects its ports 330 to port 332 and exhaust line 334, such that the two lowermost chambers 48a and b of the sleeves are deflated through the manifold, the conduit 28a, the valve ports 330 and 332, and the exhaust line 334. Also, the actuated shift valve 324 connects its port 336 to port 338 and the exhaust line 340. Accordingly, the valve 324 connects the third and fourth chambers 48c and d of the sleeves through the manifold, the conduit 28b, the valve ports 336 and 338, and the exhaust line 340 in order to deflate the third and fourth chambers at this time. Finally, the actuated valve 328 connects its port 342 to port 344 and the exhaust line 346. The actuated valve 328 connects the two uppermost chambers 48e and f in the sleeves through the manifold, the conduit 28c, the valve ports 342 and 344, and the exhaust line 346 in order to deflate the fifth and sixth chambers of the sleeves. Accordingly at the start of the deflation cycles the chambers in the sleeves are simultaneously deflated through the exhaust lines 334, 340, and 346.

When the positive output timer 316 times out, the timer 316 connects the gas supply from port 312 of valve 310 through the timer 316 to port 350 of the shift valve 310 to actuate the valve at the start of an inflation cycle. The actuated valve 310 connects its port 308 to port 352 of the valve. In turn, the gas supply is connected to port 354 of a positive output timer 356, to port 358 of a counter 360, to port 362 of shift valve 320, to port 364 of a positive output timer 366, and to port 368 of a positive output timer 370. The actuated valve 320 connects its port 372 to port 330, and, accordingly, the gas supply is connected through the flow control valve 374, the valve ports 372 and 330, the conduit 28a, and the manifold to the two lowermost chambers 48a and b of the sleeves. The flow control valve 374 serves to reduce the relatively high pressure of the gas supply utilized to actuate the pneumatic components of the controller circuitry, in order to limit the supply pressure for inflating the sleeves. Accordingly, the first pressure pulse is formed by the controller 22 at this time to inflate the first and second chambers in the sleeves.

When the positive output timer 366 times out, the timer 366 connects the gas supply at port 364 of the timer to port 376 of shift valve 324. The actuated shift valve 324 connects its port 378 to port 336 and the conduit 28b. Thus, the controller forms a second pressure pulse at this time from the first pulse, with the second pulse being supplied through the conduit 28b and the manifold to the third and fourth chambers 48c and d in the sleeves. The interval of time between formation of the first and second pressure pulses is determined by the adjustable timer 366, and the duration between the pulses may be modified by suitable adjustment of the timer 366.

When the positive output timer 370 times out, the timer 370 connects the supply through its port 368 to port 380 of the shift valve 328. The actuated shift valve 328 connects its port 382 to port 342 and the conduit 28c. Thus, the controller 22 forms the third pressure pulse at this time which passes through the conduit 28c and the manifold to the uppermost chambers 48e and f in the sleeves. As before, the third pulse is formed from the second pulse which is supplied through the conduit 28b. The interval of time between formation of the third pulse and the earlier pulses is controlled by the timer 370, and the timer 370 may be suitably adjusted to modify the duration between the pulses. Accordingly, the timed sequence of first, second, and third pulses may be modified through adjustment of the timers 366 and 370.

The counter 360 is actuated at its inlet port 358 to increment the counter 360 by one count corresponding to each inflation cycle of the controller. A user of the device may thus determine the number of inflation cycles initiated by the device during use on a patient.

When the positive output timer 356 times out, the timer 356 connects the gas supply through its port 354 to port 384 of shift valve 310 to again start a deflation cycle. As before, the deflation timer 316 is actuated at port 314 when the shift valve 310 connects the supply through valve ports 308 and 312. Also, the actuated shift valves 320, 324, and 328 connect respective conduits 28a, 28b, and 28c to the exhaust lines 334, 340, and 346 to simultaneously deflate the chambers in the sleeves while maintaining a graduated pressure gradient, as previously described. It will be seen that the timer 356 controls the duration of the inflation cycles which may be suitably modified by adjustment of the timer 356. Accordingly, the controller 22 intermittently forms a plurality of pressure pulses in a timed sequence during periodic inflation cycles, and the controller intermittently deflates the pressurized chambers in the sleeves during periodic deflation cycles which take place between the inflation cycles.

With reference to FIGS. 12-20, full length therapeutic stockings and so-called tired-leg stockings of the type including elastomer-containing yarns which exert a compressive effect on the leg portion covered by the stocking 5 boot are well known. They have been constructed extending in lengths ranging from midthigh to the gluteal furrow in a great many constructions from a great variety of elastic fabrics. They have, for instance, been made from powernet fabric, such as is described in U.S. Pat. No. 2,960,855, for example, cut to shapes resembling when relaxed the blanks of full-fashioned non-elastomeric stockings, being somewhat narrowed from such blanks. These powernet blanks and similarly shaped knitted full-fashioned stocking blanks incorporating elastomeric yarns either in the knitted stitches or inlaid in non-elastomeric yarn stitches are generally seamed up the back with various loop, flatlock or overedge stitches to form finished stockings. Circular knit stockings of non-elastomeric yarn jersey stitches with elastomer yarn inlaid therein are disclosed in the Herbert Knohl U.S. Pat. No. Re. 25,046 originally issued Dec. 6, 1960. Other circular knit constructions including jersey knit courses of elastomer-containing yarn alone and in combination with one or more course rounds of jersey stitches of non-elastomeric yarn are also well known, as are those with courses of jersey stitches and floats of elastomer-containing yarn alternating with jersey stitches of non-elastomeric yarn. Run-resistant elastic fabric stockings have also been proposed.

With regard to the compressive range of stockings presently marketed, the degree of compression exerted has been over a relatively large range. It is generally understood, however, that in a properly fitted stocking the pressure should be greater at the ankle than at the stocking top whether the stocking be possessed of the relatively reduced compression typical of therapeutic stockings used in hospitals for the prophylactic treatment of the thromboembolic disease or of so-called tired-leg stockings or of the relatively higher compression typical of stockings recommended and used in the treatment of varicosities. In these stockings the pressure has been gradually reduced from the ankle to the stocking top or upper thigh when the stocking is properly fitted in order to increase the velocity of blood flow in the leg. Full length stockings of the compressive type, regardless of the degree of compression exerted on the wearer's leg, have two problems. Because of extreme variation in the upper thigh dimensions of wearers even when other portions of the leg fall within a particular standard size range, full length stockings have been difficult to fit in the thigh area. As a result, manufacturers of non-custom stockings tend to make garments which will not bind the upper thighs of any significant proportion of wearers whose legs otherwise require a particular size stocking. The tendency, then, is to make an enlarged thigh stocking whether it is enlarged by modifying a knit full-fashioned blank or a cut powernet blank or is circular knit and enlarged by a wedge shaped insert. Such enlargement, however, sometimes causes the stocking to lose its self-support feature at the top. It is common practice to make non-elastomeric stockings self supporting by attaching a thigh encircling garter band of elastic webbing whose leg-contacting inner surface is a non-slip material such as urethane elastomer. This band may be attached under the stocking fabric but in most instances is attached in edge abutting relationship to the stocking welt, increasing the stocking length by the width of the band.

Full length stockings which have to be supported by an encircling garter band have had one undesirable feature, however. The elastic band, which is quite stiff and bears against the leg with some pressure, tends to irritate the upper inner thigh and to constrict the deep and superficial blood vessel plexus there.

A desired stocking is attained by sewing a band of the usual garterlike elastic webbing in edge abutting relationship to the stocking top welt with the band ends sewn to and separated by a wedge, fastened point downward, into a slit in the stocking upper thigh, the wedge top and the band top being aligned and forming the stocking top. The wedge which should be of a soft and readily conformable elastic fabric either in a single layer or a double layer, serves two functions. It reduces the binding in the upper thigh area when worn to a very small proportion of those who are otherwise fitted by a given size stocking, and it also constitutes the area which normally covers the deep and superficial blood vessel plexus in the upper inner thigh. The wedge may be centered in the area of the inner upper thigh but this placement necessitates the manufacture of right and left leg stockings. Optionally, the wedge may be inserted centered over the front or back fold line of the stocking from which position it may be rotated about a quarter turn to cover the inner thigh of either the right or left leg. The wedge sides are secured by sewing to the sides of the stocking slit and to the ends of the elastic webbing band by overedging or other appropriate stitching. A preferred wedge fabric is one in which elastomeric yarns are inlaid into jersey knit stitches with the elastomeric yarns extending circumferentially when the wedge is secured in place. Double fabric wedges are preferred, with the top folded edge forming a rolliresistant stocking top in the wedge area. Doubled fabric preferably should be folded so that the normal outside surface is face to face and the normal inside surface forms the wedge's outer surface. Where a single thickness of fabric is utilized for the wedge, the top edge should be a soft selvage or it should be hemmed or overedged or sealed with a soft thermoplastic to make a ravel-resistant soft edge. A very effective wedge is in the form of an equilateral triangle about 6 inches plus the garter band width on each side.

Other variations may be made from circular knit stockings with finished or welted top edges and enlarged upper thigh portions by fastening to the inside of each a webbing band, corrugated slip-resistant surface exposed, and with a gap between the ends. The top edge of the band and stocking need not be but preferably are approximately aligned.

When an elastic blank is formed either by cutting from powernet or other suitable fabric or by full-fashioned knitting, the blank may be altered to include sufficient material in the upper thigh area to prevent binding. A projection above the top of the normal blank may be made in the area intended to cover the upper inner thigh or alternatively in the front center of the blank. If the top edge is to be double, the projection should be double the width of the garter band; if single, the edge should be finished and the width should be the same as the garter band width. In this embodiment the partial circumference of elastic webbing band may be sewn in edge to edge abutting relationship to the stocking top except in the area of the projection with the bare corrugated slip-resistant surface of the band inside. Thereafter the ends of the band and the adjacent ends of the projection either in single or doubled-over form are sewn together, preferably in abutting relationship. A modification of this cut and sew or full-fashioned method involves sewing the band slip-resistant surface exposed inside a normal stocking top with a gap between the ends thereof, or if a single width projection is present, folding down the projection and sewing the projection ends to the ends of the band.

The stockings may be made adjustable in the upper thigh area by fastening means which permit that portion of the stocking top not containing the band of elastic webbing to be folded over the band and secured in place by a hook which is secured to the band and is caused to pierce the folded-over fabric. One or more separated hooks may be used but preferably a hook on either side is provided. The fabric is of loose enough construction as to permit piercing by the hook without injury.

Referring to the drawings in greater detail, FIGS. 12 and 13, illustrate respectively the inner leg side and front view of a typical circular knit stocking 410 of the invention as worn, with a foot 470 and a boot portion comprising, an ankle 472, a calf 411, a knee 418, a thigh 419, and a soft readily conformable upper thigh insert 415 made of knitted elastic fabric. The reciprocated heel 412 and the toe 413 are of typical heel and toe construction made from typical yarns preferably of stretch nylon. A partial round of elastic retention band 414 made with a corrugated slip-resistant inner surface of urethane elastomer is sewn to the upper narrow welt of the stocking proper projecting above the stocking welt so that its top forms a continuous line with the top of insert 415. The insert is overedged around its top edge and around its juncture with the slit stocking thigh 419 and with band 414 by stitching 416. The insert 415 preferably is symmetrical about the front or rear center line of the stocking so that it may be twisted in proper position to locate the insert 415 over the juncture "a" at the inner thigh, of the femoral, great saphenous, and superficial lateral cutaneous, pudendal and iliac veins. This plexus occurs approximately mid-way between the front of the thigh and the mid-inner thigh as depicted in FIG. 12.

FIG. 14 illustrates a preferred construction in which the insert wedge 415a is of doubled fabric. The fold line 415b constitutes a portion of the top edge of the stocking. The fold is preferably made with the normal fabric face folded in face to face contact.

FIGS. 13, 15 and 16 illustrate the stocking of FIG. 12 with a hook 417 which is shown sewn to a portion of the band 414 adjacent the insert 415. The hook shown disengaged in FIGS. 13 and 15 is shown in FIG. 16 engaging a folded over portion of the top margin of the insert 415. This feature, which may be incorporated on either or both sides of the insert 415, makes the upper thigh stocking portion adjustable in circumference.

Figure 17:
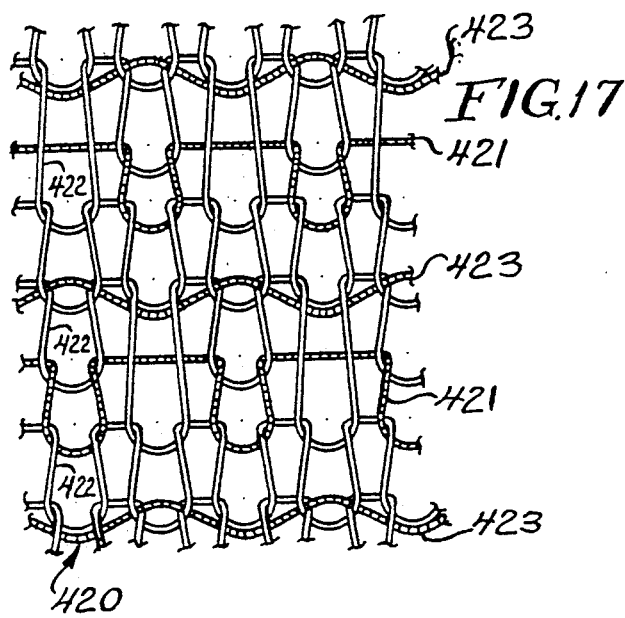
FIGS. 17–20 illustrate typical elastic fabrics including elastomeric yarns suitable for the boot portion of the stocking.

FIG. 17 shows a typical fabric 420 suitable for the stockings of the invention, in which covered elastomeric yarns 421 are formed into courses of knitted jersey stitches alternating with floats, the floats being across different wales in adjacent rounds. Yarns 422, which may be stretch synthetic yarns or usual non-stretch stocking yarns such as nylon, silk, cotton, rayon, polypropylene and the like, are formed into jersey courses. The elastomeric yarn 423 is shown inlaid into one of the jersey courses of yarn 422.

Figure 18:
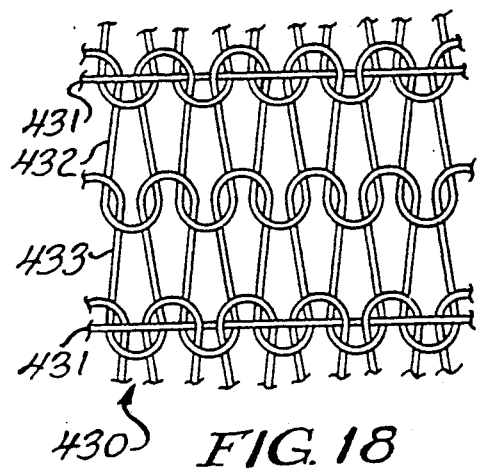

FIG. 18 is the preferred typical fabric 430 suitable for the stockings of the invention. The yarns 432 are preferably of Z-twist stretch nylon, while yarns 433 are preferably of S-twist stretch nylon but may be any non-elastomeric yarn. A covered elastomeric yarn 431 is inlaid preferably into every other course as shown but optionally in every course of jersey stitches.

Figure 19:
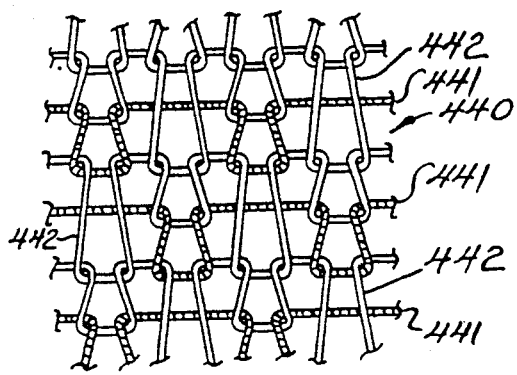

FIG. 19 is another typical fabric 440 of the invention, in which covered elastomeric yarns 441 are formed into knitted jersey stitches alternating with floats, the floats being across different wales in adjacent rounds. Yarns 442, preferably non-elastomeric stocking yarns such as synthetic or natural yarns including stretch synthetic yarns, are formed into course rounds of Jersey stitches.

Figure 20:
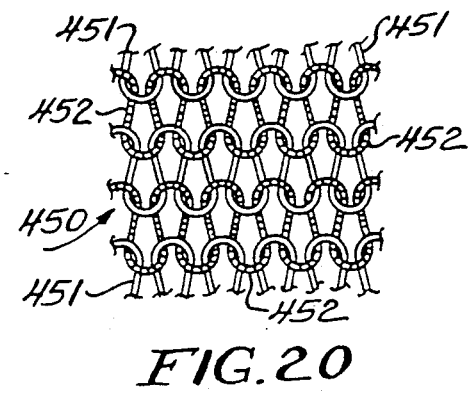

FIG. 20 is another typical fabric 450, suitable for the stockings of this invention. The jersey knit fabric has alternating rows of stitches of synthetic or natural yarns 451 and covered elastomeric yarns 452.

Using 10 filament stretch nylon 30/2 yarn, made up and knitted an automatic welt having a fully stretched circumference of 39 inches in the usual manner using a 401 needle Scott & Williams AMF 3¾ inches stocking knitting machine. Immediately after the transfer, exchanged yarns to 70/1, 17 filament Z-twist nylon 66 yarn on one feed and 70/1, 17 filament S-twist nylon 66 yarn on the other feed. Frame circumference fully stretched measured 42 inches. This frame was maintained to a point approximately at the upper calf, at which time the frame was reduced abruptly because of machine limitations but preferably within five to 10 courses to 32 inches fully stretched. This frame was maintained for approximately 120 course. The frame thereafter was gradually reduced at a constant rate by reducing stitch size until at the ankle the frame circumference measured 28 inches fully stretched. Thereafter, for 150 course rounds the frame remained at 28 inches circumference fully stretched. Thereafter the frame was gradually increased to the midpoint of the instep, at which point the frame measured 32 inches in circumference fully stretched. Thereafter a reciprocated heel was knitted in the usual manner. After completion of the heel, circular motion was resumed, the stitch being gradually reduced to a point between the heel and the toe to a circumference of 28 inches fully stretched. This circumference was maintained to the ring toe. Thereafter the ring toe including run-resist courses were knitted in the usual manner. Thereafter a reciprocated toe was knitted in the usual manner.

After the nylon frame was properly knitting, the elastomeric yarn was incorporated as follows: Immediately following completion of the top welt, the inlay feed was activated and a single covered elastomeric yarn having a 280 denier spandex core and a covering of 70/1, 34 filament stretch nylon 66 was inlaid in the course of jersey stitches knitted-off on the center feed. The elastomer should be metered in at a rate sufficient to produce a fabric having a fully stretched circumference of 38 inches. Knitting the frame including the inlaid elastomeric yarn continued at that stretched circumference to a point just above the calf, at which point the amount of metered elastomeric yarn was gradually reduced to the point at the upper calf where the circumference was 27 inches fully stretched. The elastic yarn metering rate was maintained constant for about 100 nylon courses. Thereafter the elastomeric yarn was gradually increased per round to the midpoint of the instep, at which point the stocking had a fully stretched circumference of 26 inches. At that point the elastomeric yarn was taken out and the reciprocated heel knitted. After completion of the heel, the elastomeric yarn was reintroduced in the usual manner and gradually decreased in amount per round to a point between the heel and toe, at which point the stocking foot fully stretched measured 22 inches in circumference. The elastomeric yarn was fed at this latter rate constantly for 60 course rounds, after which the elastomeric yarn rate was gradually increased to the ring toe, at which point the elastomeric yarn was taken out and the ring toe including run-resist courses were knitted in the usual manner. Thereafter a reciprocated toe was knitted and the toe opening in the sole under the base of the toes was stitched closed.

The finished stocking was preboarded at 220° F. to 230° F. for 45 seconds; the total steam treatment and drying cycle lasted approximately 2½ minutes; the total time, including build-up was about 3 minutes. (Temperatures above 240° F. are to be avoided if the most desirable products are to be obtained.) Thereafter a 1-inch wide band of typical elastic webbing of the type used for stocking garter tops was wrapped around the stocking, the corrugated slip-resistant urethane elastomer side of the band outward. The ends of the band abutted at the front fold of the stocking but were not fastened together. The top of the stocking and the top of the band were sewn together in this position by overedge stitches. The band was then folded upward so that it stood up from the stocking top, with the corrugated side in. A fastening hook, similar to those illustrated in FIGS. 13, 15, and 16 was then sewn as illustrated to each side of the band about 1½ inches from the band ends. (The distance may be anywhere from three-fourths inch to 2 inches.) The stocking was then slit between the band ends along the front fold for about 6 inches. A diamond shaped piece of the same fabric as the stocking boot and about 6 inches across and 13 inches long, with the inlaid elastomeric yarn running transversely, was folded to make substantially equilateral triangle of doubled fabric. This triangular double-fabric wedge was inserted into the slit in the stocking, point downward, with its folded edge in alignment with the top of the band, and was overedge stitched, as is illustrated in FIG. 14 to the sides of the slit in the stocking and to the ends of the band of elastic webbing to complete the stocking.

Figure 21:
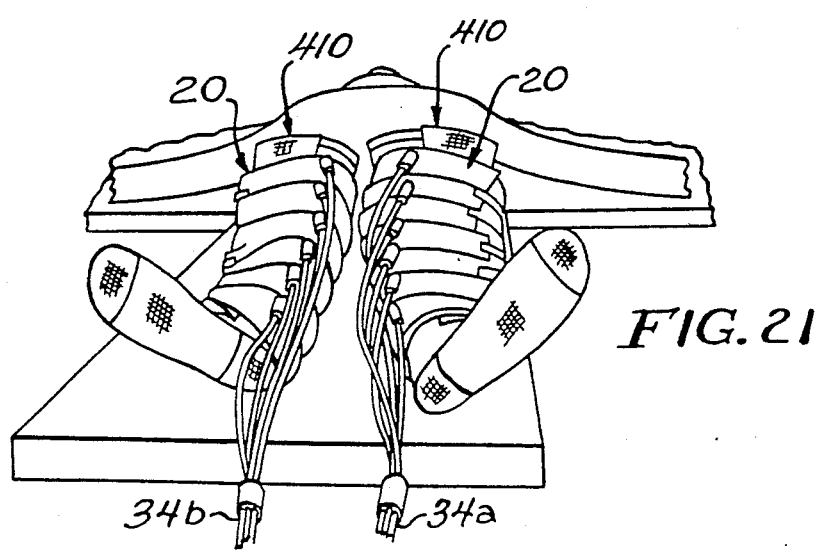
FIG. 21 is a perspective view of a pair of compression sleeves used in the sequential intermittant compression device and a pair of stockings beneath the sleeves of the present invention.
Figure 22:
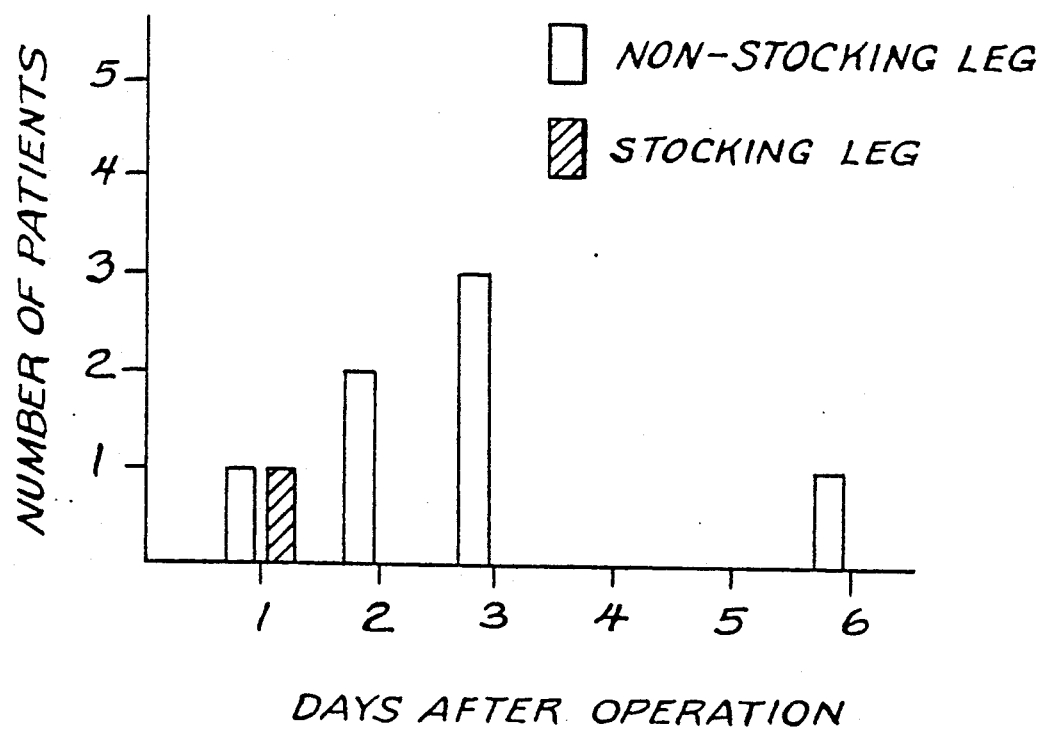
FIG. 22 is a histogram showing the day on which DVT was first detected in a stocking leg and a non-stocking leg.

With regard to FIG. 21, according to the present invention, the elastic compression stockings 410 are first placed on the limbs, and the sequential compression device 20 or intermittent pneumatic compression (IPC) is placed over the stockings 410, and both are used simultaneously on the limbs. A study was conducted to assess the prophylactic effectiveness for postoperative deep venous thrombosis (DVT) of a regimen employing the simultaneous use of graduated elastic compression stockings and IPC compared to a regimen of IPC alone.

PATIENTS AND METHODS

The study population was a consecutive group of patients undergoing general surgical procedures and without any condition which would make them unsuitable for scanning with the I-125 fibrinogen uptake test. Seventy-eight patients were studied, and all patients gave their informed consent for participating in the study.

The mean age of the 43 male patients was 62.4 years (±11.1 years), while the mean age of the 35 female patients was 59.7 years (±12.9 years).

The distribution of patients on the basis of age is illustrated in Table I. These groupings as a function of age are reflective of those typically encountered in this department and are consistent with those as reported in previous efficacy studies. A summary of operative procedures is given in Table II. Approximately one third of the patients were having operations for malignant disease and only seven of these procedures were considered palliative.

As the duration of anesthesia has been previously shown to be correlatable to risk for DVT development in the surgical patient, Table III provides a distribution of patients as a function of the duration of anesthesia. The mean duration of anesthesia was 72 minutes (±29 minutes). In addition to venous stasis during anesthesia, postoperative immobility is significant in the assessment of overall risk for DVT development. Immobility is defined as the number of days required before the patient is able to ambulate unaided. The mean period of immobility for the study population was 64 hours (±14 hours).

On hospital admission, all patients were properly sized and fitted with graduated elastic compression stockings, (Thigh Length TED, a trademark of The Kendall Company). At the time of surgery, one graduated compression stocking was removed from either the right or the left leg (randomly allocated), and Intermittent Pneumatic Sequential Compression (sequential compression device SCD or IPC with full leg sleeves sold by The Kendall Company) was applied to both legs. The randomization of graduated compression stockings resulted in its application to right legs 51% of the time and to left legs 49% of the time. The SCD remained until the patient was fully ambulant. At the time the SCD was discontinued, the previously removed graduated compression stocking was reapplied and all patients continued to wear graduated compression stockings on both extremities for the remainder of the study period.

All patients were assessed preoperatively for the presence of DVT using Doppler ultrasound and strain gauge plethysmography for maximum venous outflow measurements. Any positive sign for DVT preoperatively would exclude the patient from the study. Postoperative diagnosis for DVT was conducted with dual screening approaches with any positive diagnosis being confirmed with contrast venography. The I-125 fibrinogen uptake test was performed on the first, third, fifth, and seventh days after operation, using the Pitman isotope localization monitor. A sustained difference of more than 20 percent between adjacent sites on the leg was diagnostic of DVT, and the patient underwent contrast venography for clot confirmation.

To complement the I-125 fibrinogen uptake test, the patient also underwent Doppler ultrasound and maximum venous outflow assessment by strain gauge plethysmography between the fifth and seventh post-operative day. Again, a positive finding with either Doppler or strain gauge would be followed by contrast venographic confirmation.

RESULTS

The overall incidence of DVT in the patients studies was 9%. Results demonstrate complete agreement between the I-125 diagnosis and the contrast venography diagnosis. In addition, there were no proximal vein thrombi detected. This finding is not surprising in view of the fact that full-leg compression prophylaxis was in use across all of the patients in the study, and the fact that the intensive diagnostic surveilence allowed early treatment of any confirmed distal DVT to prevent propagation. No pulmonary embolii were diagnosed in any of the study patients.

Results from the alternate leg comparison in Table IV are categorized on a unilateral-bilateral basis. Of the untied cases, all six of the DVT were found in the non-stocking leg. There was 0% incidence of DVT in the stocking leg and 7.7% incidence in the non-stocking leg. The exact P-value for this finding is 0.0156 which is a statistically significant result.

The day of onset for the DVT is indicated in FIG. 1. The only DVT diagnosis made during the first postoperative day was the single bilateral case and reflects a patient with gastric carcinoma plus secondaries. The remaining DVT, all unilateral in the non-stocking leg, were diagnosed on days two through six.

DISCUSSION

Only one patient in this series developed a deep venous thrombosis in a stocking leg, and this was associated with bilateral venous thrombosis. In all the other patients studied the venous thrombosis occurred in the non-stocking leg. The onset of venous thrombosis occurs more commonly after the second postoperative day, a finding in keeping with previous investigations. From this study it would appear that the application of a graduated compression stocking beneath the sequential compression device is more effective in preventing deep venous thrombosis than SCD alone.

The methodology of this study does not exclude the possibility of an effect of one graduated elastic compression stocking on the blood flow in the opposite leg. However, results from similar risk patient populations relative to the demonstration of efficacy of graduated compression in alternate leg series studies have been shown to be highly consistent with results demonstrating efficacy of graduated compression in alternate patient studies. An assessment of this correlation demonstrates homogeneity in trial results relative to prophylactic effectiveness. Therefore, it is argued that the design of this study to answer the fundamental question of testing the simultaneous use of graduated elastic compression and intermittent pneumatic compression is appropriate.

The results are surprising as both compression modalities have previously been thought to produce prophylactic effects in large part by reducing venous stasis via increasing linear blood flow velocity and decreasing venous blood clearance time. In terms of linear blood flow velocity, in was demonstrated by Doppler ultrasound at the femoral vein in the inguinal ligament that graduated elastic compression stockings produced an average increase of 20% over base line. Using radiopaque dye methodology, an average increase was previously measured in linear blood flow velocity of 33% over base line with graduated elastic compression stockings.

On the other hand, it was previously demonstrated that intermittent sequential pneumatic compression produces an increase of 240% in blood flow velocity as measured by Doppler ultrasound at the femoral vein. A comparison of these measurements by earlier investigators clearly demonstrates that intermittent sequential pneumatic compression increases linear blood velocity far in excess of that produced by graduated elastic compression stockings. Therefore, if linear blood flow velocity were the only factor involved in the prophylactic mechanism for compression, then one would not expect the striking result relative to DVT formation demonstrated in this study. However, it was previously demonstrated that other hemodynamic parameters, namely venous capacitance and venous outflow, are significantly diminished from preoperative conditions to postoperative conditions.

While care must be taken in the interpretation of these data, the findings of this study in conjunction with the hemodynamic results from earlier investigations raise an important consideration of the mechanism by which graduated elastic compression stockings reduce DVT.

It was reported in animal model experiments a direct relationship between venodilation and endothelial damage, as well as, a direct relationship between venodilation and postoperative DVT in human subjects. These correlations and earlier canine model investigations provide a new appreciation of Virchow's Triad and in particular a new understanding of the interrelationship between venous stasis and vein wall injury. It is suggested that venous stasis, as induced by surgery, can result in large changes in vein diameters with concomitant production of mechanical stress to induce microtears in the endothelial layer. The subsequent site of endothelial damage provides a location to potentiate the clotting process.

During anesthesia and postoperative bed rest, venous dilation may occur as a result of muscle tone changes and concomitant changes in venous capacitance. Intermittent pneumatic compression compresses the veins but for a relatively short period of time with a concomitant large increase blood flow velocity. It is possible that graduated compression stockings, while providing continuous stimulation of linear blood flow velocity also prevent dilation of the venous system in the lower extremities and reduce an additional aspect of thrombogenicity, namely the exposure of collagen.

This study indicates that the combined regimen of graduated elastic compression stockings with intermittent sequential pneumatic compression is a more effective prophylactic regimen than intermittent pneumatic compression alone

TABLE I

| AGE DISTRIBUTION OF PATIENTS | | |
|---|---|---|
| | Number of Patients | |
| Years of Age | Male | Female |
| 40-50 | 8 | 12 |
| 51-60 | 5 | 6 |
| 61-70 | 18 | 6 |
| 71-80 | 11 | 9 |
| Over 80 | 0 | 2 |

TABLE II

| OPERATIONS PERFORMED | | |
|---|---|---|
| | Malignant | Benign |
| Cholecystectomy | 0 | 26 |
| Colon Resections | 7 | 3 |
| Splenectomy | 4 | 2 |
| Gastric Procedures | 3 | 5 |
| Laparotomies | 6 | 6 |
| Incisional Hernias | 0 | 8 |
| Other | 4 | 4 |

TABLE III

| DURATION OF ANESTHESIA | |
|---|---|
| | Number of Patients |
| Less than 1 hour | 17 |
| 1 to 2 hours | 50 |
| 2 to 3 hours | 11 |
| Greater than 3 hours | 0 |

TABLE IV

| INCIDENCE OF DVT | | | |
|---|---|---|---|
| | Unilateral | Bilateral | Total |
| Non-Stocking Legs | (78) 6(7.7%) | 1 | 7(9%) |

TABLE IV-continued

| INCIDENCE OF DVT | | | |
|---|---|---|---|
| | Unilateral | Bilateral | Total |
| Stocking Legs | (78) 0(0%) | 1 | 1(1%) |

$p = 0.0156$ (McNemar's exact test)

SUMMARY

The incidence of deep venous thrombosis (DVT) was assessed in a series of seventy-eight patients undergoing major surgical operations to compare the prophylactic effectiveness of intermittent sequential pneumatic compression alone to the simultaneous use of graduated compression stockings with intermittent sequential pneumatic compression. The diagnosis of DVT was determined with the I-125 fibrinogen uptake test, Doppler ultrasound, maximum venous outflow by strain gauge plethysmography and contrast venography. The incidence of DVT in non-stocking legs was 9% while that in the stocking legs was 1%. The simultaneous use of graduated elastic compression stockings with intermittent pneumatic compression (IPC) is more effective than IPC alone in the reduction postoperative DVT.

The foregoing detailed description is given for clearness of understanding only, and no unnecessary limitations should be understood therefrom, as modifications will be obvious to those skilled in the art.

What is claimed is:

1. A device for applying compressive pressures against a patient's limb, comprising in combination:
   a stocking having a circumferential elastic boot portion which applied a compressive pressure against the limb which pressure decreases from the ankle to a top of the stocking;
   an elongated pressure sleeve for enclosing a length of the patient's limb over the stocking, said sleeve having a plurality of separate fluid pressured chambers progressively arranged longitudinally along the sleeve from a lower portion of the limb to an upper portion of the limb proximal the patient's heart relative to said lower portion;
   means for forming a plurality of fluid pressure pulses; and
   means for connecting the pressure pulses to chambers in the sleeve such that a compressive pressure is applied against the patient's limb by a sleeve which pressure decreases from the lower to upper limb portions.

2. The device of claim 1 including means for forming pressure pulses in a timed sequence during periodic compression cycles.

3. The device of claim 2 wherein the pressure pulses are connected to separate chambers in the sleeve in an arrangement with later pulses in said sequence being connected to more upwardly located chambers in the sleeve.

4. The device of claim 1 including means for intermittently connecting the chamber to an exhaust means during a periodic decompression cycle between a compression cycle.

5. The device of claim 1 wherein the stocking extends to a location adjacent the thigh region of the patient.

6. The device of claim 5 wherein the stocking has an elastic band having a pair of ends, with the ends of the band being separated by an area of soft conformable elastic fabric which extends downwardly from the top of the stocking for a substantial distance below the band for covering the plexus of deep and superficial blood vessels in the upper thigh of the patient.

* * * * *